United States Patent
Hubbell et al.

(10) Patent No.: US 12,281,071 B2
(45) Date of Patent: Apr. 22, 2025

(54) SYSTEMS AND METHODS FOR ENHANCING THE RECOVERY OF STYRENE

(71) Applicant: T.EN Process Technology, Inc., Houston, TX (US)

(72) Inventors: Douglas S. Hubbell, Sudbury, MA (US); Slawomir A. Oleksy, Billerica, MA (US)

(73) Assignee: T.EN Process Technology, Inc., Houston, TX (US)

( * ) Notice: Subject to any disclaimer, the term of this patent is extended or adjusted under 35 U.S.C. 154(b) by 0 days.

(21) Appl. No.: 17/870,821

(22) Filed: Jul. 22, 2022

(65) Prior Publication Data

US 2024/0026231 A1  Jan. 25, 2024

(51) Int. Cl.
| | |
|---|---|
| C07C 7/00 | (2006.01) |
| C07C 7/05 | (2006.01) |
| C10G 31/06 | (2006.01) |
| C10G 31/08 | (2006.01) |

(52) U.S. Cl.
CPC ............. *C07C 7/00* (2013.01); *C07C 7/005* (2013.01); *C07C 7/05* (2013.01); *C10G 31/06* (2013.01); *C10G 31/08* (2013.01); *C10G 2300/1096* (2013.01); *C10G 2300/4012* (2013.01); *C10G 2300/807* (2013.01); *C10G 2400/30* (2013.01)

(58) Field of Classification Search
None
See application file for complete search history.

(56) References Cited

U.S. PATENT DOCUMENTS

| | | | |
|---|---|---|---|
| 3,469,617 A | | 9/1969 | Palmason |
| 3,515,647 A | * | 6/1970 | Van Tassell ............... C07C 7/05 |
| | | | 159/13.4 |

(Continued)

FOREIGN PATENT DOCUMENTS

| | | | |
|---|---|---|---|
| CN | 101337860 A | * | 1/2009 |
| EP | 0650977 A1 | | 5/1995 |

(Continued)

OTHER PUBLICATIONS

Machine translation CN101337860. Retrieved Apr. 28, 2023 (Year: 2023).*

*Primary Examiner* — In Suk C Bullock
*Assistant Examiner* — Alyssa L Cepluch
(74) *Attorney, Agent, or Firm* — Troutman Pepper Locke LLP; Gabrielle L. Gelozin

(57) ABSTRACT

A method for enhancing the recovery of styrene includes feeding a hot liquid residue stream to a stripping vessel from a styrene monomer purification finishing system. The hot liquid residue stream includes styrene and compounds less volatile than styrene. The method includes introducing a gas to the stripping vessel to strip a portion of the styrene as vapor, generating a vaporized styrene portion, returning the vaporized styrene portion and the gas to the styrene monomer purification finishing system, recovering at least a portion of the vaporized styrene portion into a styrene monomer product, and producing a final liquid residue stream from a bottom of the stripping vessel with a lower concentration of styrene than the hot liquid residue stream feeding the stripping vessel.

16 Claims, 2 Drawing Sheets

(56) References Cited

U.S. PATENT DOCUMENTS

| | | | | |
|---|---|---|---|---|
| 4,177,110 A | * | 12/1979 | Watson | .................... C07C 7/05 |
| | | | | 203/91 |
| 4,197,400 A | | 4/1980 | Wollrab et al. | |
| 4,469,558 A | * | 9/1984 | Watson | .................... C07C 7/05 |
| | | | | 203/84 |
| 4,529,753 A | | 7/1985 | Taylor | |

FOREIGN PATENT DOCUMENTS

| | | |
|---|---|---|
| WO | 199948931 A1 | 9/1999 |
| WO | 2017067887 A1 | 4/2017 |

\* cited by examiner

SYSTEMS AND METHODS FOR ENHANCING THE RECOVERY OF STYRENE

TECHNICAL FIELD

The present disclosure relates to improvements on a method to recover a styrene product and systems to recover the styrene product. Specifically, the systems and methods of the present disclosure reduce utility cost, improve efficiency, and provide savings in comparison with the current methods practiced in the industry.

BACKGROUND

It is well known in the art of styrene monomer manufacturing to have the crude styrene from a dehydrogenation section stripped of compounds lighter than styrene in one or more distillation columns, hereinafter collectively referred to as a styrene prefractionation system. The remaining stream, including styrene monomer and less volatile impurities, is fed to a styrene monomer purification finishing system, which typically starts with a distillation finishing column that operates under vacuum and recovers a final styrene monomer product as distillate. The heavier impurities in this stream include C9 aromatics (such as propylbenzenes and methylstyrenes), C10 aromatics (such as diethylbenzene and divinylbenzene isomers), multiple-ring aromatics which are less volatile than styrene (primarily condensation products of styrene, including stilbene), and styrene polymer.

The bottoms stream from the distillation finishing column is typically partially vaporized in a steam-heated exchanger and fed to a residue flash drum where the vapor is separated from the liquid and fed back to the distillation finishing column. This residue flash drum liquid contains most of the low-volatility (heavy) by-products of the styrene process as well as residual styrene typically at a concentration of about 5 wt %. A portion of this liquid from the residue flash drum can be optionally recycled to the start of the styrene prefractionation system upstream of the distillation finishing column to reuse residual active polymerization inhibitors. The rest of the liquid is the net heavy by-product stream (residue) of the styrene process, and the styrene content in this stream is a yield loss for the process.

U.S. Pat. No. 3,515,647 describes a system similar to what is described above; however, the residue flash drum and the steam-heated exchanger upstream of it are replaced by a thin-film evaporator with a steam-heated jacket, which provides the same function. This prior art has an option of using a hot gaseous stream fed to the thin-film evaporator to assist in the stripping of styrene from the net residue. However, the evaporator vaporizes a relatively large amount of styrene and other components such that the hot gaseous stream must be relatively large to have much impact on the separation. Using large amounts of nitrogen or steam, as recommended, would be costly and would require changes to the overhead system of the distillation finishing column to separate out the added component from the styrene monomer product.

At least for economic reasons, it is desirable to have a process with a lower yield loss of the styrene monomer. Thus, the inventive methods disclosed herein efficiently minimize styrene product loss to the heavy by-product residue stream, while also reducing energy costs.

SUMMARY

A method for enhancing the recovery of styrene includes feeding a hot liquid residue stream to a stripping vessel from a styrene monomer purification finishing system. The hot liquid residue stream includes styrene and compounds less volatile than styrene. The method includes introducing a gas to the stripping vessel to strip a portion of the styrene as vapor, generating a vaporized styrene portion. The method includes returning the vaporized styrene portion and the gas to the styrene monomer purification finishing system. The method includes recovering at least a portion of the vaporized styrene portion into a styrene monomer product. The method includes producing a final liquid residue stream from a bottom of the stripping vessel with a lower concentration of styrene than the hot liquid residue stream feeding the stripping vessel.

The stripping vessel can operate at a temperature lower than the hot liquid residue stream. The gas can be a non-condensable at ambient temperatures and pressures, such as natural gas, nitrogen, or air. The gas can also be steam.

In some embodiments, the stripping vessel operates under vacuum. The method can include recycling part of the liquid residue stream from the bottom of the stripping vessel back to the start of a styrene prefractionation system, upstream of the styrene monomer purification finishing system. The liquid residue leaving the stripping vessel can be at a temperature between about 250° F. and 340° F. Introducing the gas to the stripping vessel can include at least one of (i) feeding the gas to the stripping vessel separately from the liquid residue stream, or (ii) feeding the gas to the hot liquid residue stream and then to the stripping vessel. In some embodiments, feeding the hot liquid residue stream includes feeding the hot liquid residue stream to a top of the stripping vessel and wherein introducing the gas includes introducing the gas to the bottom of the stripping vessel.

A system for enhancing recovery of styrene from a residue stream is also disclosed. The system includes a stripping vessel configured and adapted to receive a hot liquid residue feed from a styrene monomer purification finishing system.

In some embodiments, the system includes a return conduit connected to the stripping vessel configured and adapted to feed a portion of the styrene contained in the hot liquid residue feed to a front of a styrene prefractionation system. The stripping vessel can be a drum configured and adapted to receive a stripping gas either directly to the drum or to a hot liquid residue feed line and then to the drum. The stripping vessel can also be a stripper column with packing and/or trays. A top of the stripper column is configured and adapted to receive the hot liquid residue feed, wherein a bottom of the stripper column is configured and adapted to receive a stripping gas feed.

The stripping vessel can be a drum with no internal elements to enhance gas-liquid contacting. The stripping vessel can contain internal elements to enhance gas-liquid contacting. The internal elements inside the stripping vessel can be distillation trays. The internal elements inside the stripping vessel can be distillation packing. The gas can be either steam, natural gas, nitrogen, or air. The stripping vessel can be configured and adapted to facilitate contact between a hot liquid residue feed from a styrene monomer purification finishing system and a gas to recover a portion of styrene contained in the liquid feed. The stripping vessel can include an outlet configured and adapted to return a portion of styrene contained in a hot liquid residue feed to a front of a styrene prefractionation system.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject invention appertains will readily understand how to make and use the devices and methods of the subject invention without undue experimentation, preferred embodiments thereof will be described in detail herein below with reference to certain figures, wherein.

DETAILED DESCRIPTION

Figure 2:
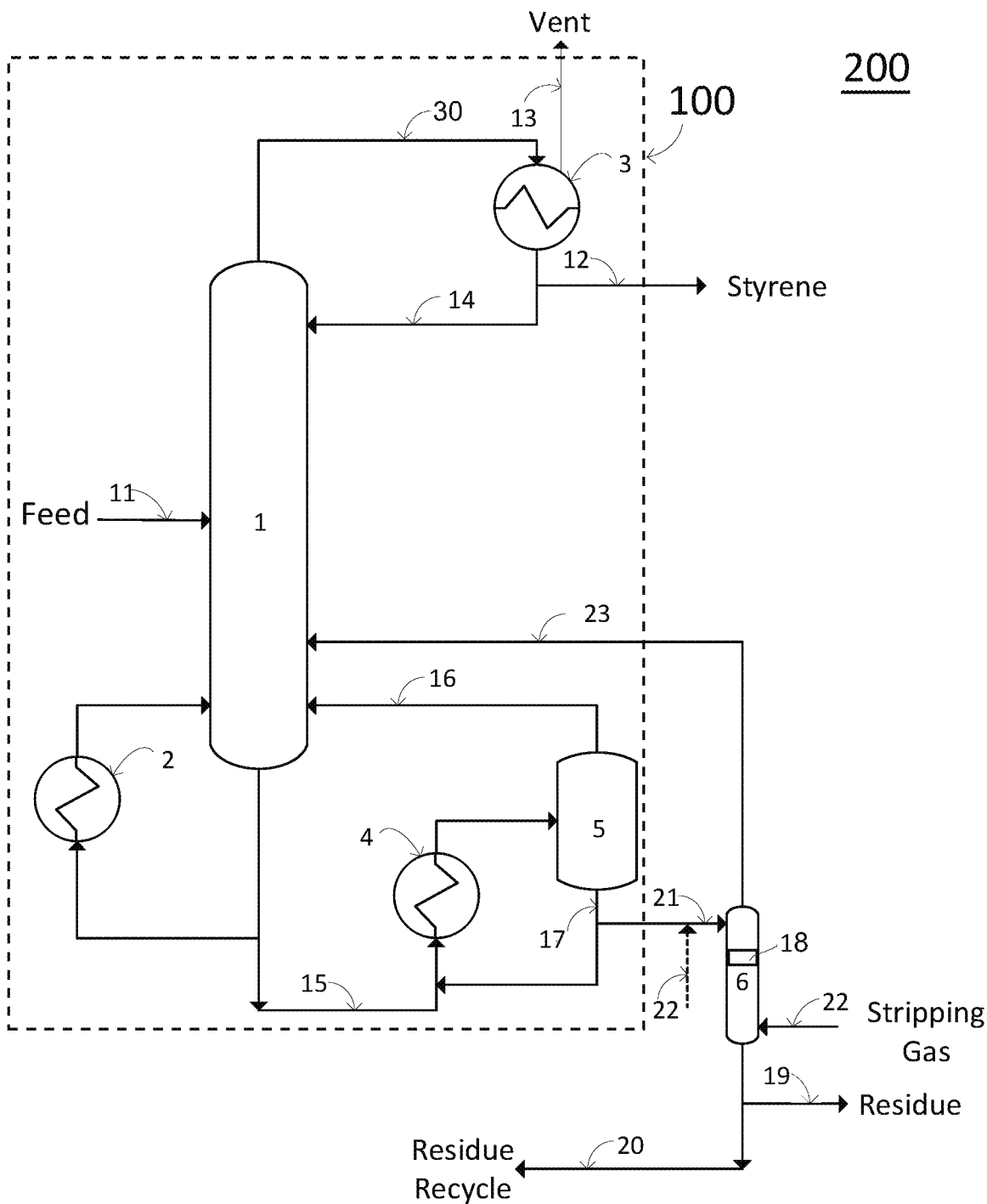
FIG. 2 is a schematic view of a styrene monomer purification finishing and stripping system constructed in accordance with an embodiment of the present disclosure.

Referring now to the appended drawings, wherein like reference numerals identify similar structures or features of the subject invention, there is illustrated in FIG. 2 a new and useful styrene monomer purification finishing and stripping system constructed in accordance with a preferred embodiment of the subject disclosure and designated generally by reference numeral 200. Styrene monomer purification finishing and stripping system 200 includes a new stripping vessel, which results in lower heat input into the styrene monomer purification finishing and stripping system 200 and lower yield loss of styrene monomer than traditional systems.

Figure 1:
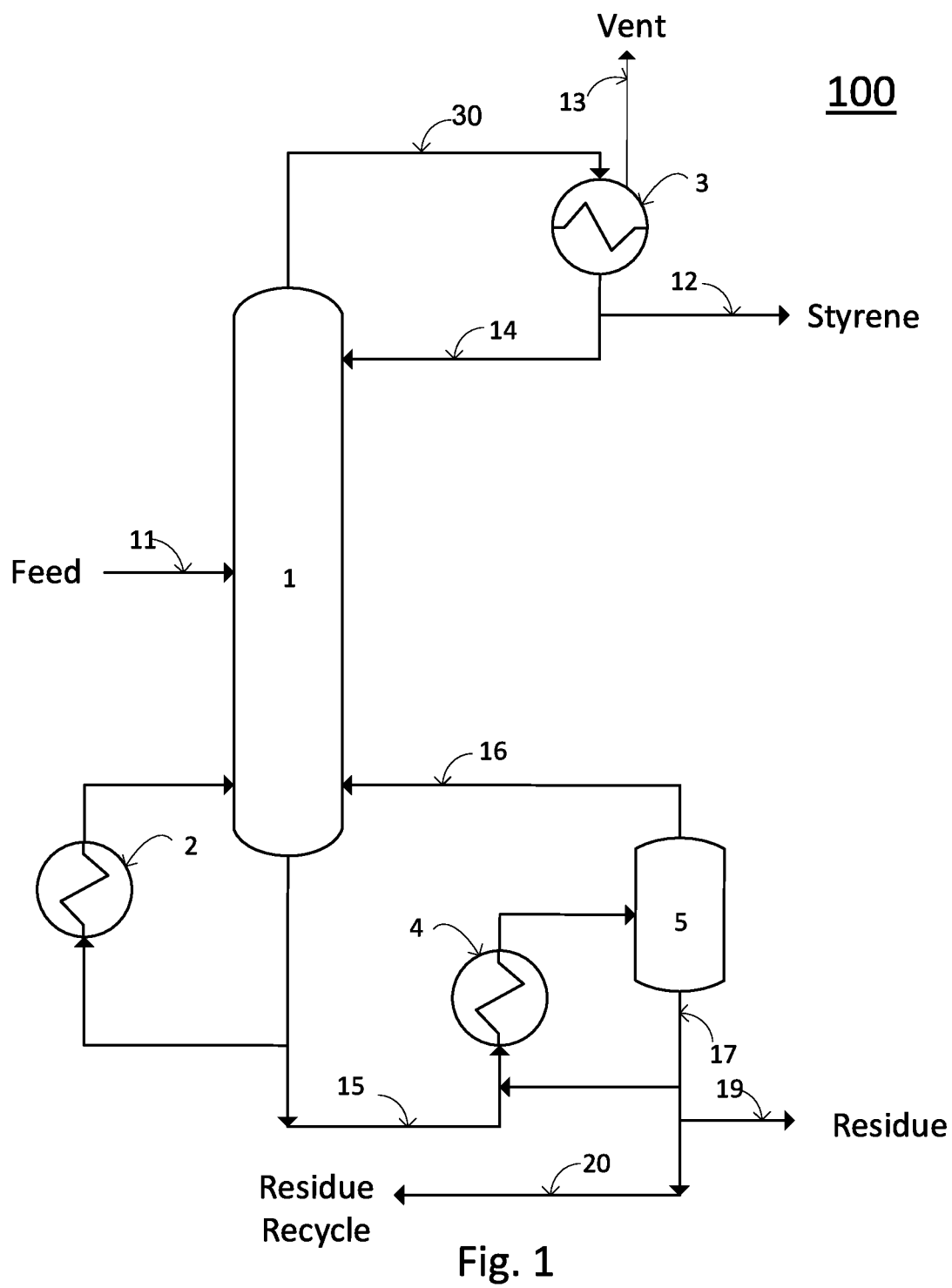
FIG. 1 is a schematic view of a prior art styrene monomer purification finishing system.

FIG. 1 shows a prior art styrene monomer purification finishing system designated by reference numeral 100. Prior art styrene monomer purification finishing system 100 is located downstream of a styrene prefractionation system which comprises one or more distillation columns that remove and recover lighter compounds from the crude styrene from the dehydrogenation section of the styrene process. This styrene monomer purification finishing system 100 includes a distillation finishing column 1 which receives a feed 11 from the styrene prefractionation system. Feed 11 includes styrene monomer, methylstyrenes, polystyrene and other heavy compounds. An overhead vapor stream 30 from the distillation finishing column is partially condensed in a condenser 3 producing a vapor distillate stream 13, a liquid distillate stream 12 (styrene monomer product) and a column reflux stream 14. Heat to the distillation finishing column is provided by a steam reboiler 2. A liquid bottoms stream 15 from the distillation finishing column 1 flows to a steam-heated exchanger (residue reboiler) 4. The partially vaporized bottoms stream from the residue reboiler 4 is fed to a residue flash drum 5 where the liquid and vapor streams are separated. The vapor stream 16 is returned to the distillation finishing column 1, and the liquid stream 17 exits the residue flash drum 5. A portion 20 of the liquid stream 17 is optionally recycled to the beginning of the styrene prefractionation system, and the remaining liquid is the net heavy by-product residue stream 19 from the styrene monomer process.

The distillation finishing column 1 and residue flash drum 5 operate at deep vacuum, which results in low operating temperatures that minimize both the loss of styrene polymerizing to form polymer and the consumption of polymerization inhibitors. Column 1 internals can include either all trays, distillation packing above the feed and trays below the feed, or all packing. Compared to trays, packing has the advantages of lower pressure drop, which results in lower temperatures, less liquid hold-up (both of which reduce the loss of styrene to polymer), and smaller column diameters. In contrast, trays are less expensive internals, are less likely to have poor performance due to flow maldistribution, are less prone to fouling by insoluble polymer, and are easier to clean of polymer. Having packing above the feed and trays below the feed is the preferred design for the distillation finishing column 1 because this configuration provides the partial benefit of lower pressures and lower liquid hold-up with packing while providing trays where polymer fouling is most likely.

To further reduce the styrene concentration in the residue using the current system, as shown in FIG. 1, one would typically increase the temperature from to the residue reboiler 4. However, excessively high residue temperatures can degrade the polymerization inhibitors in the residue. Instead, as shown in FIG. 2, stripping styrene from the residue with a gas in an additional downstream stripping vessel 6 and feeding the gas with recovered styrene back to the styrene monomer purification finishing system is disclosed. This disclosure further provides a cost-effective means for reducing the loss of styrene to the residue in a styrene plant without having excessive temperatures that can degrade the polymerization inhibitors.

FIG. 2 shows a styrene monomer purification finishing and stripping system 200 constructed in accordance with an embodiment of the disclosure. The styrene monomer purification finishing and stripping system 200 in FIG. 2 includes system 100 of FIG. 1 and has a hot liquid residue stream 21 of net liquid stream 17 from residue of a flash drum 5 fed to stripping vessel 6 where it is contacted with stripping gas 22 to remove a portion of the styrene from the liquid. In FIG. 2, stripping gas 22 is shown being fed separately from hot liquid residue stream 21. Feeding the liquid 21 to the top and the gas 22 to the bottom typically only applies when the stripping vessel 6 is a stripper column, i.e., a vessel with trays or packing (internal elements 18), described in more detail below. As an alternative embodiment, shown with an arrow in broken lines, stripping gas 22 can be fed into hot liquid residue stream 21 and then fed to stripping vessel 6. The gas mixture with recovered styrene 23 from the stripping vessel 6 is routed to the distillation finishing column 1. A portion of the stripping vessel liquid residue bottoms stream (schematically depicted by line 20) is optionally recycled to the beginning of the styrene prefractionation system and the remaining liquid is the net heavy by-product residue stream 19 from the styrene monomer process.

Since a styrene monomer purification finishing and stripping system 200 operates under vacuum, the system design typically has an allowance for air leakage from the atmosphere into the equipment and piping, and a vacuum system is used to remove the air and maintain a constant vacuum pressure at the top of the distillation finishing column. The flowrate of air, natural gas, or nitrogen gas needed in the stripping vessel 6 can be small relative to the typical allowance for air leakage into the design. Although the injection of gas decreases the air-leakage capacity of the vacuum system, the decrease in capacity is typically minimal, and no additional equipment is normally required for the styrene monomer purification finishing and stripping system in FIG. 2 compared with the prior art system in FIG. 1.

The stripping gas 22 can also be steam. In this case, the styrene monomer product 12 will contain dissolved water. If the quantity of injected steam is large enough, then a separate liquid water phase can form in the overhead reflux vessel (not shown) and also possibly in any vessel used to store or transport the styrene. Any water phase with the styrene product would typically need to be separated off before the styrene is used.

Utilizing air instead of nitrogen or natural gas in the stripping vessel 6 has a further advantage in that it reduces loss of styrene to polymer in the system because the presence of oxygen enhances the effectiveness of the polymerization inhibitor 4-tertiary-butylcatechol (TBC) that is added typically to the distillation finishing column reflux 14. The sizes of the stripping vessel 6 and the associated pump are very small relative to the equipment in the prior art styrene monomer purification finishing system.

With continued reference to FIG. 2, the stripping vessel 6 could be either a simple vapor-liquid separation drum or a stripper column with contacting internal elements 18 below the liquid feed. In terms of performance, the stripper column is preferable to a simple drum. In a stripper column with the residue flash drum liquid introduced at the top and the stripping gas added at the bottom of the stripper column, contacting internal elements 18 such as trays or packing result in counter-current stripping of the styrene from the liquid, which can significantly reduce the amount of gas needed for a certain amount of styrene removal from the residue. The gas strips out a portion of the styrene from the residue and returns it to the distillation finishing column 1 by way of return line 23 to an optimum entry point. Since the gas is diluting the styrene in the vapor phase from the stripping vessel 6, the equilibrium temperature of the liquid from the residue flash drum 5 drops when it enters the stripping vessel 6 and contacts the stripping gas. This drop in liquid temperature provides the heat for vaporizing styrene in the liquid from the residue flash drum 5.

Given below are three tables with simulation results for the styrene monomer purification finishing system in a base line process (Table 1), a process with the embodiment of the stripping vessel as a drum (a simple vapor-liquid separator) (Table 2), and the improved process with a further embodiment of the stripping vessel as a stripper column (Table 3). All of these simulations are based on the production of 125,000 lb/hr of final styrene monomer product and a distillation finishing column with packing above the feed and trays below the feed. Air is used as the stripping gas for the results in Table 2 and Table 3. Use of nitrogen instead of air would produce virtually identical results since air is composed of mostly of (79 vol %) nitrogen and has very similar physical properties. Steam and natural gas have physical properties that are different from nitrogen or air, but since the gas flow is so small relative to the liquid feed to the stripping vessel, an equal molar flow of steam or natural gas gives essentially the same effect on the equilibrium as nitrogen or air.

Additionally, the process described above does not require the stripping gas to be heated. Since the flow of stripping gas is small relative to that in U.S. Pat. No. 3,515,647, the benefit to heating the gas would be negligible.

Table 1 shows results for the prior art process shown in FIG. 1 when the styrene concentration is reduced in the net residue. As shown, the temperature of the residue in the residue flash drum rises significantly as the styrene content in the residue is decreased and the duty of the residue reboiler increases. With 5.0 wt % styrene in the residue, the residue flash drum is operated at a temperature of about 324° F. (162° C.). Reducing the styrene concentration to 2.0 wt % in the residue requires an increase of the residue flash drum temperature to 358° F. (181° C.). However, at least one commercially available inhibitor degrades at this temperature. Thus, reducing this yield loss to 2.0 wt % in the residue flash drum results in excessively high temperatures that degrade the polymerization inhibitor in the residue.

TABLE 1

| | | | | | | |
|---|---|---|---|---|---|---|
| Styrene in Residue | wt % | 5.0 | 4.0 | 3.0 | 2.0 | 1.0 |
| Styrene in Finishing Column Bottoms | wt % | 56.9 | 50.9 | 43.2 | 32.7 | 18.9 |
| Styrene in Residue Flash Drum Liquid | wt % | 5.0 | 4.0 | 3.0 | 2.0 | 1.0 |
| Finishing Column Bottom Temperature | ° F. | 214.9 | 218.1 | 223.0 | 230.7 | 245.3 |
| Residue Flash Drum Temperature | ° F. | 324.3 | 333.7 | 345.0 | 358.0 | 374.7 |
| Finishing Column Reboiler Duty | millions of BTU/hr | 18.01 | 18.01 | 18.01 | 18.01 | 18.01 |
| Residue Reboiler Duty | millions of BTU/hr | 6.72 | 6.73 | 6.70 | 6.80 | 6.83 |
| Column Condenser Duty | millions of BTU/hr | 31.23 | 31.23 | 31.20 | 31.29 | 31.31 |
| Styrene Loss to Residue | lb/hr | 28.3 | 22.4 | 16.6 | 11.0 | 5.4 |

Table 2 shows results for the improved process of this disclosure with the embodiment of a single-stage stripping drum utilizing air as the stripping medium. In comparison to Table 1, the temperature of the residue flash drum is lower, and the stripping drum temperature is lower than the residue flash drum temperature for all concentrations of styrene in the net residue in Table 2. The gas can be fed directly to the stripping drum, as shown in FIG. 2, but it is preferable to feed the gas into the residue line feeding the drum, as shown with the dashed line in FIG. 2. Results with nitrogen, natural gas, or steam as the stripping gas would be nearly identical for the same molar flow of stripping gas.

TABLE 2

| | | | | | | |
|---|---|---|---|---|---|---|
| Styrene in Residue | wt % | 5.0 | 4.0 | 3.0 | 2.0 | 1.0 |
| Styrene in Finishing Column Bottoms | wt % | 58.4 | 56.3 | 53.2 | 48.2 | 37.4 |
| Styrene in Residue Flash Drum Liquid | wt % | 5.4 | 5.3 | 5.0 | 4.6 | 3.6 |
| Finishing Column Bottom Temperature | ° F. | 214.0 | 214.9 | 216.1 | 218.1 | 222.8 |
| Residue Flash Drum Temperature | ° F. | 320.0 | 320.0 | 320.0 | 320.0 | 320.0 |
| Stripping Drum Temperature | ° F. | 317.5 | 311.7 | 304.5 | 294.3 | 275.7 |
| Finishing Column Reboiler Duty | millions of BTU/hr | 18.01 | 18.01 | 18.01 | 18.01 | 18.01 |

TABLE 2-continued

| | | | | | | |
|---|---|---|---|---|---|---|
| Residue Reboiler Duty | millions of BTU/hr | 6.80 | 6.74 | 6.68 | 6.56 | 6.56 |
| Column Condenser Duty | millions of BTU/hr | 31.32 | 31.27 | 31.21 | 31.06 | 30.95 |
| Styrene Loss to Residue | lb/hr | 28.4 | 22.5 | 16.7 | 10.9 | 5.4 |
| Stripping Air Flow | lb/hr | 0.6 | 7.5 | 28.6 | 88.9 | 306.7 |
| Styrene in Stripping Drum Vapor | lb/hr | 25.5 | 87.9 | 173.0 | 315.1 | 658.2 |

Table 3 shows results for a further embodiment of the improved process of this disclosure, with a stripper column as the stripping vessel utilizing air as the stripping gas. The stripper column has multiple stages, with the liquid feed from the residue flash drum entering the top of the stripper column and the air entering the bottom of the stripper column. In comparing Tables 2 and 3 for the cases with 2.0 wt % styrene in the net residue, it is shown that going from a one-stage stripping drum (fourth data column in Table 2) to a two-stage stripper column (third data column in Table 3) reduces the stripping air required by 63% (from 87.6 lb/hr to 32.2 lb/hr). The last three columns in Table 3 illustrate that adding additional stripper stages reduces the stripping gas consumption or lowers the amount of styrene lost in the final residue at the same flow of stripping gas.

TABLE 3

| Number of Stages | | 2 | 2 | 2 | 2 | 4 | 6 |
|---|---|---|---|---|---|---|---|
| Styrene in Residue | wt % | 4.0 | 3.0 | 2.0 | 1.0 | 1.0 | 1.0 |
| Styrene in Finishing Column Bottoms | wt % | 56.9 | 53.7 | 49.1 | 40.0 | 42.5 | 43.5 |
| Styrene in Residue Flash Drum Liquid | wt % | 5.3 | 5.0 | 4.7 | 3.9 | 4.1 | 4.2 |
| Finishing Column Bottom Temperature | ° F. | 214.7 | 215.8 | 217.8 | 221.7 | 220.5 | 220.1 |
| Residue Flash Drum Temperature | ° F. | 320.0 | 320.0 | 320.0 | 320.0 | 320.0 | 320.0 |
| Stripper Bottoms Temperature | ° F. | 311.7 | 305.4 | 297.7 | 285.4 | 289.0 | 289.9 |
| Stripper Overhead Temperature | ° F. | 315.3 | 311.9 | 307.4 | 300.4 | 307.4 | 309.2 |
| Finishing Column Reboiler Duty | millions of BTU/hr | 18.01 | 18.01 | 18.01 | 18.01 | 18.01 | 18.01 |
| Residue Reboiler Duty | millions of BTU/hr | 6.61 | 6.69 | 6.68 | 6.62 | 6.66 | 6.58 |
| Column Condenser Duty | millions of BTU/hr | 31.14 | 31.23 | 31.23 | 31.16 | 31.21 | 31.14 |
| Styrene Loss to Residue | lb/hr | 22.4 | 16.7 | 11.0 | 5.4 | 5.4 | 5.4 |
| Stripping Air Flow | lb/hr | 4.1 | 12.8 | 32.3 | 83.6 | 42.1 | 33.9 |

By stripping styrene from the residue with gas in the stripping vessel and feeding the gas with stripped styrene back to the distillation finishing column, the loss of styrene to the residue is significantly reduced without the need to operate at higher temperatures.

The systems and methods of the present disclosure, as described above and shown in the drawings, provide means of economically recovering styrene from the heavy by-product stream in a styrene plant without exceeding temperature degradation limitations for the polymerization inhibitors. Each of the systems and methods described above are based on a single finishing column, followed by a residue flash drum, and followed by a stripping vessel with stripping gas. While the apparatus and methods of the subject disclosure have been shown and described with reference to embodiments, those skilled in the art will readily appreciate that changes and/or modifications to what is upstream of the stripping vessel may be made thereto without departing from the spirit of the subject disclosure.

What is claimed is:

1. A method for recovery of residual styrene, comprising:
    recovering a hot liquid residue stream from a flash drum of a styrene monomer purification finishing system,
        wherein the hot liquid residue stream comprises residual styrene, and
        wherein the styrene monomer purification finishing system comprises a distillation column upstream of the flash drum;
    feeding the hot liquid residue stream and a gas to a stripping vessel downstream of the flash drum to produce a vaporized styrene stream and a final liquid residue stream,
        wherein the final liquid residue stream has a lower concentration of styrene than the hot liquid residue stream; and
    returning the vaporized styrene stream to the distillation column to obtain a styrene monomer product.

2. The method of claim 1, wherein the stripping vessel operates at a temperature lower than the hot liquid residue stream.

3. The method of claim 1, wherein the gas is noncondensable at ambient temperatures and pressures.

4. The method of claim 1, wherein the gas is steam, natural gas, nitrogen, or air.

5. The method of claim 1, wherein the stripping vessel operates under vacuum.

6. The method of claim 1, further comprising recycling part of the final a liquid residue stream from the bottom of the stripping vessel to a start of a styrene prefractionation system, upstream of the styrene monomer purification finishing system.

7. The method of claim 1, wherein the final liquid residue stream leaving the stripping vessel is at a temperature between about 250° F. and 340° F.

8. The method of claim 1, wherein feeding the gas to the stripping vessel includes at least one of (i) feeding the gas to the stripping vessel separately from the hot liquid residue stream, or (ii) feeding the gas to the hot liquid residue stream and then to the stripping vessel.

9. The method of claim 1, wherein the feeding comprises feeding the hot liquid residue stream to the top of the stripping vessel and the gas to the bottom of the stripping vessel.

10. A method for recovery of residual styrene, comprising:
recovering a hot liquid residue stream comprising residual styrene from a flash drum of a styrene monomer purification finishing system; and
passing the hot liquid residue stream and a stripping gas to a multi-stage stripping vessel downstream of the flash drum to generate a vaporized styrene stream, wherein the stripping gas is air.

11. The method of claim 10, wherein the stripping gas is introduced into the multi-stage stripping vessel separately from the hot liquid residue stream.

12. The method of claim 10, wherein the stripping gas is introduced into the hot liquid residue stream downstream of the flash drum and upstream of the multi-stage stripping vessel.

13. The method of claim 10, wherein the styrene monomer purification finishing system further includes a distillation column, and wherein the method further comprises:
returning the vaporized styrene stream the distillation column; and
recovering a styrene monomer product from the distillation column.

14. The method of claim 13, further comprising:
producing a final liquid residue stream from a bottom of the stripping vessel, wherein the final liquid residue stream has a lower concentration of styrene than the hot liquid residue stream feeding the multi-stage stripping vessel.

15. The method of claim 10, further comprising:
producing a final liquid residue stream from a bottom of the stripping vessel, wherein the final liquid residue stream has a lower concentration of styrene than the hot liquid residue stream feeding the multi-stage stripping vessel.

16. A method for recovery of residual styrene, comprising:
recovering a product from a styrene prefractionation system;
passing the product as a feed to a distillation column of a styrene monomer purification finishing system;
passing a liquid bottoms stream from the distillation column to a flash drum to obtain a hot liquid residue stream comprising residual styrene;
feeding the hot liquid residue stream and air into a stripping vessel to produce a vaporized styrene stream and a final liquid residue stream,
wherein the final liquid residue stream has a lower concentration of styrene than the hot liquid residue stream; and
returning the vaporized styrene stream to the distillation column to obtain a styrene monomer product.

* * * * *